(12) United States Patent
Lee et al.

(10) Patent No.: US 10,502,683 B2
(45) Date of Patent: Dec. 10, 2019

(54) PHOTODETECTOR SELECTION APPARATUS AND METHOD AND SCATTERING COEFFICIENT MEASUREMENT APPARATUS AND METHOD

(71) Applicants: SAMSUNG ELECTRONICS CO., LTD., Suwon-si (KR); Korea University Research and Business Foundation, Seoul (KR)

(72) Inventors: Joon Hyung Lee, Seongnam-si (KR); Beop Min Kim, Seoul (KR); Jung Yong Nam, Hwaseong-si (KR); Ki Young Chang, Yongin-si (KR); Zephaniah Phillips, V, Seoul (KR); Seung Ho Paik, Seongnam-si (KR)

(73) Assignees: SAMSUNG ELECTRONICS CO., LTD., Suwon-si (KR); Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/028,028

(22) Filed: Jul. 5, 2018

(65) Prior Publication Data
US 2019/0033212 A1  Jan. 31, 2019

(30) Foreign Application Priority Data

Jul. 27, 2017 (KR) .................. 10-2017-0095558

(51) Int. Cl.
*G01N 21/49* (2006.01)
*H04B 5/00* (2006.01)
(Continued)

(52) U.S. Cl.
CPC .......... *G01N 21/49* (2013.01); *A61B 5/1455* (2013.01); *A61B 5/14546* (2013.01);
(Continued)

(58) Field of Classification Search
CPC .... G01N 21/49; G01N 21/4738; G01N 21/94; A61B 5/14546; A61B 5/1455; H01L 25/167; H04B 5/0031
(Continued)

(56) References Cited

U.S. PATENT DOCUMENTS 5,477,051 A   12/1995  Tsuchiya
5,676,142 A   10/1997  Miwa et al.
(Continued)

FOREIGN PATENT DOCUMENTS

JP   6-221913 A   8/1994
JP   7-323033 A   12/1995
(Continued)

*Primary Examiner* — Roy M Punnoose
(74) *Attorney, Agent, or Firm* — Sughrue Mion, PLLC

(57) ABSTRACT

A photodetector selection apparatus and method and a scattering coefficient measurement apparatus and method are provided. The photodetector selection apparatus for measuring a scattering coefficient may include: a light source configured to emit light to a subject; a photodetector array configured to detect the light that is reflected or scattered from the subject and measure a light intensity of the detected light; and a processor configured to select at least one photodetector from a plurality of photodetectors of the photodetector array, based on a change in the measured light intensity of each of the plurality of photodetectors according to a change in a scattering coefficient of the subject, and determine the scattering coefficient of the subject based on the light intensity that is measured by the selected at least one photodetector.

28 Claims, 11 Drawing Sheets

(51) Int. Cl.
*H01L 25/16* (2006.01)
*G01N 21/47* (2006.01)
*A61B 5/145* (2006.01)
*A61B 5/1455* (2006.01)
*G01N 21/94* (2006.01)

(52) U.S. Cl.
CPC ....... *G01N 21/4738* (2013.01); *H01L 25/167* (2013.01); *H04B 5/0031* (2013.01); *G01N 21/94* (2013.01)

(58) Field of Classification Search
USPC .......................................................... 356/343
See application file for complete search history.

(56) References Cited

U.S. PATENT DOCUMENTS

| | | | |
|---|---|---|---|
| 5,694,931 A | 12/1997 | Tsuchiya | |
| 5,867,807 A * | 2/1999 | Yamada | G01N 21/49 702/22 |
| 6,078,833 A | 6/2000 | Hueber | |
| 6,606,509 B2 | 8/2003 | Schmitt | |
| 6,794,670 B1 * | 9/2004 | Folestad | G01J 3/4412 250/573 |
| 7,532,919 B2 | 5/2009 | Soyemi et al. | |
| 9,554,709 B2 | 1/2017 | Fukutani | |
| 2006/0043007 A1 * | 3/2006 | Tarumi | A61M 1/3621 210/96.2 |
| 2010/0076319 A1 * | 3/2010 | Mannheimer | A61B 5/14551 600/476 |
| 2014/0012103 A1 * | 1/2014 | Nishida | A61B 5/1455 600/316 |
| 2014/0046165 A1 | 2/2014 | Fukutani | |
| 2015/0313516 A1 * | 11/2015 | Shimizu | G01N 21/4795 600/322 |
| 2017/0067823 A1 | 3/2017 | Tseng | |
| 2017/0100039 A1 | 4/2017 | Fukutani | |
| 2018/0132718 A1 * | 5/2018 | Nam | A61B 5/0008 |
| 2018/0132766 A1 * | 5/2018 | Lee | G01N 21/474 |

FOREIGN PATENT DOCUMENTS

| | | |
|---|---|---|
| JP | 8-94517 A | 4/1996 |
| JP | 2003-50200 A | 2/2003 |
| JP | 3433534 B2 | 5/2003 |
| JP | 2009-85712 A | 4/2009 |
| JP | 2015-80604 A | 4/2015 |
| JP | 5783779 | 9/2015 |
| KR | 10-2007-0082928 A | 8/2007 |
| KR | 10-2015-0093088 A | 8/2015 |

* cited by examiner

PHOTODETECTOR SELECTION APPARATUS AND METHOD AND SCATTERING COEFFICIENT MEASUREMENT APPARATUS AND METHOD

CROSS-REFERENCE TO RELATED APPLICATION(S)

This application claims priority from Korean Patent Application No. 10-2017-0095558, filed on Jul. 27, 2017 in the Korean Intellectual Property Office, the disclosure of which is incorporated herein by reference in its entirety.

BACKGROUND

1. Field

Apparatuses and methods consistent with exemplary embodiments relate to a scattering coefficient measurement technology.

2. Description of Related Art

A scattering coefficient may indicate a ratio of an amount of scattered light to the total amount of input light, and it is widely used in various fields since the constituent material of a subject can be analyzed by using the scattering coefficient.

With regard to a medium (e.g., human body) having a high degree of turbidity, it may be important to select a photodetector at an optimal position in order to increase a sensitivity to the change in scattering coefficient. However, until now, there is no definite criterion for selecting the photodetector at the optimal position, and it is difficult to measure an accurate scattering coefficient.

SUMMARY

Exemplary embodiments address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided a photodetector selection apparatus for measuring a scattering coefficient, the photodetector selection apparatus including: a light source configured to emit light to a subject; a photodetector array configured to detect the light that is reflected or scattered from the subject and measure a light intensity of the detected light; and a processor configured to select at least one photodetector from a plurality of photodetectors of the photodetector array, based on a change in the measured light intensity of each of the plurality of photodetectors according to a change in a scattering coefficient of the subject, and determine the scattering coefficient of the subject based on the light intensity that is measured by the selected at least one photodetector.

The processor may select a first photodetector and a second photodetector from the plurality of photodetectors, wherein an increased amount of the measured light intensity of the first photodetector, which is measured while the scattering coefficient changes, may be greater than an increased amount of the measured light intensity of any other photodetector in the photodetector array, and a decreased amount of the measured light intensity of the second photodetector, which is measured while the scattering coefficient changes, may be greater than a decreased amount of the measured light intensity of any other photodetector in the photodetector array.

The processor may calculate a photodetector-specific representative function that represents the change in the measured light intensity of each of the plurality of photodetectors, calculate a photodetector-specific measurement error for the photodetector-specific representative function, correct the photodetector-specific representative function based on the calculated photodetector-specific measurement error, and select the first photodetector and the second photodetector from the photodetector array based on the corrected photodetector-specific representative function.

The processor may calculate the photodetector-specific representative function through a regression analysis.

The photodetector-specific measurement error for the photodetector-specific representative function may be an extent that a measured light intensity of each specific photodetector deviates from a linearity of a representative function of the specific photodetector.

The processor may calculate scattering-coefficient-specific errors of each of the plurality of photodetectors by comparing intensities measured by each of the plurality of photodetectors for each scattering coefficient with intensities obtained through a representative function of a corresponding photodetector, and calculates the photodetector-specific measurement error by summing the scattering-coefficient-specific errors of each plurality of photodetectors.

The processor may correct a slope of the photodetector-specific representative function based on the calculated photodetector-specific measurement error.

The processor may correct the slope of the photodetector-specific representative function by subtracting the photodetector-specific measurement error from the slope of the photodetector-specific representative function or by dividing the slope of the photodetector-specific representative function by the photodetector-specific measurement error.

The processor may select a photodetector having a greatest positive slope of a photodetector-specific representative function as the first photodetector and a photodetector having a greatest negative slope of a photodetector-specific representative function as the second photodetector.

A distance between the light source and the first photodetector may be shorter than a distance between the light source and the second photodetector.

The processor may divide the photodetector array into a plurality of photodetector sets according to a distance from the light source, and select, from the plurality of photodetector sets, a first photodetector set a second photodetector set, wherein an increased amount of the measured light intensity of the first photodetector set, which is measured while the scattering coefficient changes, may be greater than an increased amount of the measured light intensity of any other photodetector set in the photodetector array, and a decreased amount of the measured light intensity of a second photodetector set, which is measured while the scattering coefficient changes, may be greater than a decreased amount of the measured light intensity of any other photodetector set in the photodetector array.

The processor may calculate a photodetector-specific representative function that represents the change in the measured light intensity of each of the plurality of photodetectors, calculate a photodetector-specific measurement error for the photodetector-specific representative function, correct a slope of the photodetector-specific representative function based on the calculated photodetector-specific measurement error, divide the photodetector array into a plurality of photodetector sets according to a distance from the light source, calculate an average slope of each of the plurality of photodetector sets by averaging slopes of corrected photodetector-specific representative functions of photodetectors in each of the plurality of photodetector sets, and select a first photodetector set and a second photodetector set from the photodetector array based on the calculated average slope of each of the plurality of photodetector sets.

The processor may select a photodetector set having a greater positive average slope as the first photodetector set and select a photodetector set having a greatest negative average slope as the second phothodetector set.

A distance between the light source and the first photodetector set may be shorter than a distance between the light source and the second photodetector set.

According to an aspect of another exemplary embodiment, there is provided a photodetector selection method for calculating a scattering coefficient, the photodetector selection method including: measuring, by each of a plurality of photodetectors, a light intensity of a light that is emitted to and then reflected or scattered from a subject; and selecting at least one photodetector from the plurality of photodetectors for measuring a scattering coefficient from a photodetector array based on a change in the measured light intensity of each of the photodetectors according to a change in a scattering coefficient of the subject.

The selecting the at least one photodetector may include selecting a first photodetector and a second photodetector from the plurality of photodetectors, an increased amount of the measured light intensity of the first photodetector, which is measured while the scattering coefficient changes, is greater than a increased amount of the measured light intensity of any other photodetector in the photodetector array, and a decreased amount of the measured light intensity of the second photodetector, which is measured while the scattering coefficient changes, is greater than a decreased amount of the measured light intensity of any other photodetector in the photodetector array.

The selecting the plurality of photodetectors may include calculating a photodetector-specific representative function that represents the change in the measured light intensity of each of the plurality of photodetectors, calculating a photodetector-specific measurement error for the photodetector-specific representative function, correcting the photodetector-specific representative function based on the calculated photodetector-specific measurement error, and selecting the first photodetector and the second photodetector from the photodetector array based on the corrected photodetector-specific representative function.

The calculating the photodetector-specific representative function may include calculating the photodetector-specific representative function through a regression analysis.

The photodetector-specific measurement error for the photodetector-specific representative function may be an extent that a measured light intensity of each specific photodetector deviates from a linearity of a representative function of the specific photodetector.

The calculating the photodetector-specific measurement error may include calculating scattering-coefficient-specific errors of each of the plurality of photodetectors by comparing intensities measured by each of the plurality of photodetectors for each scattering coefficient with intensities obtained through a representative function of a corresponding photodetector and calculating the photodetector-specific measurement error by summing the scattering-coefficient-specific errors of each plurality of photodetectors.

The correcting the photodetector-specific representative function may include correcting a slope of the photodetector-specific representative function based on the calculated photodetector-specific measurement error.

The correcting the photodetector-specific representative function may include correcting the slope of the photodetector-specific representative function by subtracting the photodetector-specific measurement error from the slope of the photodetector-specific representative function or by dividing the slope of the photodetector-specific representative function by the photodetector-specific measurement error.

The selecting the first photodetector and the second photodetector may include selecting a photodetector having a greatest positive slope of a photodetector-specific representative function as the first photodetector and a photodetector having a greatest negative slope of a photodetector-specific representative function as the second photodetector.

A distance between the light source and the first photodetector may be shorter than a distance between the light source and the second photodetector.

The selecting of the plurality of photodetectors may include dividing the photodetector array into a plurality of photodetector sets according to a distance from the light source, and selecting, from the plurality of photodetector sets, a first photodetector set and a second photodetector, wherein an increased amount of the measured light intensity of the first photodetector set, which is measured while the scattering coefficient changes, is greater than an increased amount of the measured light intensity of any other photodetector set in the photodetector array, and a decreased amount of the measured light intensity of a second photodetector set, which is measured while the scattering coefficient changes, is greater than a decreased amount of the measured light intensity of any other photodetector set in the photodetector array.

The selecting the plurality of photodetectors may include calculating a photodetector-specific representative function that represents the change in the measured light intensity of each of the plurality of photodetectors, calculating a photodetector-specific measurement error for the photodetector-specific representative function, correcting a slope of the photodetector-specific representative function based on the calculated photodetector-specific measurement error, dividing the photodetector array into a plurality of photodetector sets according to a distance from the light source, calculating an average slope of each of the plurality of photodetector sets by averaging slopes of corrected photodetector-specific representative functions of photodetectors in each of the plurality of photodetector sets, and selecting a first photodetector set and a second photodetector set from the photodetector array on the basis of the calculated average slope of each of the plurality of photodetector sets.

The selecting the first photodetector set and the second photodetector set may include selecting a photodetector set having a greatest positive average slope as the first photodetector set and a photodetector set having a greatest negative average slope as the second photodetector set.

A distance between the light source and the first photodetector set may be shorter than a distance between the light source and the second photodetector set.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
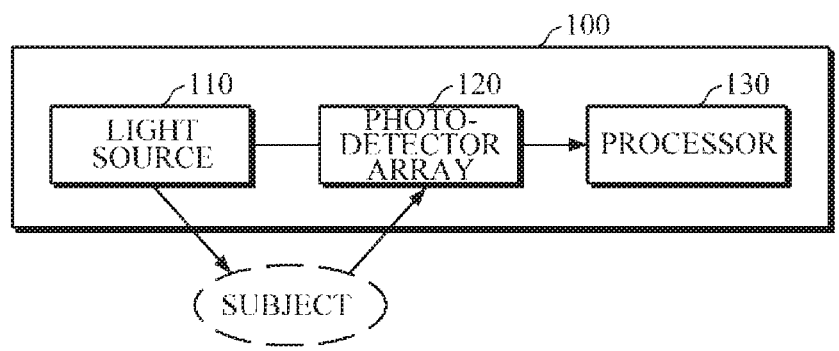
FIG. 1 is a block diagram illustrating one embodiment of a photodetector selection apparatus.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Respective operations described herein may be performed in a different order than that which is explicitly described. In other words, the respective steps may be performed in the same order as described, simultaneously, or in a reverse order.

Unless the context clearly indicates otherwise, the singular forms include the plural forms. It should be understood that the terms "comprises" or "includes" specify some features, numbers, steps, operations, elements, and/or combinations thereof when used herein, but do not preclude the presence or possibility of one or more other features, numbers, steps, operations, elements, and/or combinations thereof in addition to the description.

Expressions such as "at least one of," when preceding a list of elements, modify the entire list of elements and do not modify the individual elements of the list.

FIG. 1 is a block diagram illustrating one embodiment of a photodetector selection apparatus.

The photodetector selection apparatus 100 is an apparatus for selecting a photodetector to be used in measuring a scattering coefficient from among a plurality of photodetectors, and may be mounted in an electronic device. The electronic device may include a mobile phone, a smartphone, a tablet computer, a notebook computer, a personal digital assistant (PDA), a portable multimedia player (PMP), a navigation system, an MP3 player, a digital camera, and a wearable device, and the wearable device may include various types, such as a wristwatch type, a wrist band type, a ring type, a belt type, a necklace type, an ankle band type, a thigh band type, a forearm band type, and the like. However, the electronic device and the wearable device are not limited to the aforementioned examples.

Referring to FIG. 1, the photodetector selection apparatus 100 may include a light source 110, a photodetector array 120, and a processor 130.

The light source 100 may emit light to a subject. For example, the light source 110 may emit light of a predetermined wavelength, for example, near infrared (NIR), to the subject. However, the wavelength of light to be emitted from the light source 110 may vary according to the measurement purpose or the type of constituent element to be measured. In addition, the light source 110 may not necessarily be configured with a single light emitting object and may be configured with a set of a plurality of light emitting objects. In the case in which the light source 110 is configured with a set of a plurality of light emitting objects, the plurality of light emitting objects may each emit light of a different wavelength or light of the same wavelength according to the measurement purpose. According to an exemplary embodiment, the light source 110 may be a light emitting diode (LED) or a laser diode, but aspects of the present disclosure are not limited thereto.

The photodetector array 120 may include a plurality of photodetectors. Each of the photodetectors may detect light reflected or scattered from the subject and measure intensity of the detected light. According to an exemplary embodiment, the photodetector may include a photodiode, a photo transistor (PTr), or a charge-coupled device (CCD).

The processor 130 may select a plurality of photodetectors to be used in measuring a scattering coefficient from the photodetector array 120 on the basis of a change in the intensity measured by each photodetector according to the change in scattering coefficient.

According to an exemplary embodiment, the processor 130 may select, from the photodetector array 120, a first photodetector a second photodetector under the following conditions: the processor 130 may select the first photodetector if an increased amount of a light intensity, which is measured by the first photodetector while the scattering coefficient of the subject changes, is greater than an increased amount of a light intensity that is measured by any other photodetector set in the photodetector array 120; and the processor 130 may select the second photodetector if a decreased amount of a light intensity, which is measured by the second photodetector while the scattering coefficient of the subject changes, is greater than an decreased amount of a light intensity that is measured by any other photodetector in the photodetector array 120. A detailed description thereof will be provided below with reference to FIG. 2.

According to another embodiment, the processor 130 may divide the photodetector array 120 into a plurality of photodetector sets according to a distance from the light source 110, and may select, from the plurality of photodetector sets, a photodetector set whose measured intensity increases the most when the scattering coefficient of the subject changes and select a photodetector set whose measured intensity decreases the most when the scattering coefficient of the subject changes. In this case, one or more photodetectors having the same distance from the light source 110 may be included in the same set. A detailed description thereof will be provided below with reference to FIG. 4.

Figure 2:
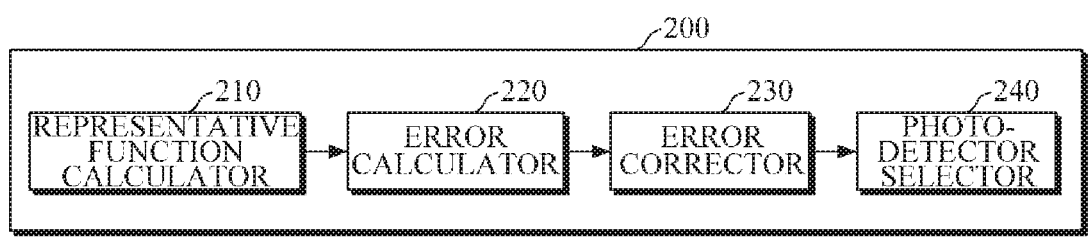
FIG. 2 is a block diagram illustrating one embodiment of a processor.

FIG. 2 is a block diagram illustrating one embodiment of a processor. A processor 200 of FIG. 2 may be one embodiment of the processor 130 of FIG. 1.

Referring to FIG. 2, the processor 200 includes a representative function calculator 210, an error calculator 220, an error corrector 230, and a photodetector selector 240.

The representative function calculator 210 calculates a representative function (hereinafter referred to as a "photodetector-specific representative function") representing the change in the measured intensity of each photodetector according to the change in scattering coefficient, on the basis of the change in the scattering coefficient of the subject and the corresponding change in the measured intensity of each photodetector. According to an exemplary embodiment, the representative function calculator 210 may calculate a regression equation for the change in measured intensity of each photodetector through a regression analysis and use the calculated regression equation as the representative function of the photodetector.

The error calculator 220 may calculate a measurement error (hereinafter referred to as a "photodetector-specific measurement error") for the representative function of each photodetector. In this case, the extent that the measured intensity of each photodetector deviates from the linearity of the representative function may be defined as the photodetector-specific measurement error for the representative function of each of the photodetectors.

According to an exemplary embodiment, the error calculator 220 may compare the intensities measured by each photodetector for each scattering coefficient with intensities obtained from the representative function of the photodetector to calculate scattering-coefficient-specific errors of each photodetector, and calculate the photodetector-specific measurement error by summing the calculated scattering-coefficient-specific errors of each photodetector.

For example, under the assumption that, when scattering coefficients of a subject are µs1, µs2, and µs3, intensities measured by a photodetector PD1 are R1, R2, and R3 and predicted intensities obtained through the representative function of the photodetector PD1 are R1', R2', and R3', the error calculator 220 may calculate error E1 (E1=|R1'−R1|) for scattering coefficient µs1, error E2 (E2=|R2'−R2|) for scattering coefficient µs2, and error E3 (E3=|R3'−R3|) for scattering coefficient µs3, and calculate a measurement error Ea(=E1+E2+E3) of the photodetector PD1. Such an error calculation process may be performed for each of the photodetectors in the photodetector array.

The error calculator 230 may correct the representative function of each photodetector calculated by the representative function calculator 210 using the error calculated by the error calculator 220 for each corresponding photodetector.

According to an exemplary embodiment, the error corrector 230 may correct a photodetector-specific representative function by subtracting a photodetector-specific measurement error from a slope of the photodetector-specific representative function. For example, when the representative function of the photodetector PD1 is y=9x+5 and an error is 3, the error corrector 230 may correct the representative function of the photodetector PD1 to a function of y=6x+5 by subtracting the error 3 from the slope 9.

According to another embodiment, the error corrector 230 may correct a photodetector-specific representative function by dividing a slope of the photodetector-specific representative function by a photodetector-specific measurement error. For example, when a representative function of the photodetector PD1 is y=9x+5 and an error is 3, the error corrector 230 may correct the representative function of the photodetector PD1 to a function of y=3x+5 by dividing the slope, 9, by the error, 3.

Meanwhile, the above-described examples of correcting the photodetector-specific representative function are only some embodiments, and aspects of the present disclosure are not limited thereto.

The photodetector selector 240 may select two photodetectors used in measuring a scattering coefficient from the photodetector array on the basis of the corrected photodetector-specific representative functions.

According to an exemplary embodiment, the photodetector selector 240 may select a photodetector (hereinafter referred to as a "first photodetector") having the largest positive slope of a photodetector-specific representative function and a photodetector (hereinafter referred to as a "second photodetector") having the largest negative slope of a photodetector-specific representative function. For example, when the photodetector array includes four photodetectors PD1, PD2, PD3, and PD4, a slope of a corrected representative function of the photodetector PD1 is +9, a slope of a corrected representative function of the photodetector PD2 is +5, a slope of a corrected representative function of the photodetector PD3 is −1 and a slope of a corrected representative function of the photodetector PD4 is −4, the photodetector selector 240 may select the photodetector PD1, which has the largest positive slope (+9) of the corrected representative function, and the photodetector PD4, which has the largest negative slope (−4) of the corrected representative function, to be used in measuring a scattering coefficient.

According to an exemplary embodiment, a distance between the light source and the first photodetector may be shorter than a distance between the light source and the second photodetector. That is, the photodetector selector 240 may select the first photodetector, which has the largest positive slope of the corrected representative function, at a distance close to the light source and select the second photodetector, which has the largest negative slope of the corrected representative function, at a distance far from the light source. However, the description given above is merely one embodiment, and aspects of the present disclosure are not limited thereto. That is, the distance between the light source and the first photodetector may be greater than the distance between the light source and the second photodetector according to the performance and use of a system.

Figure 3:
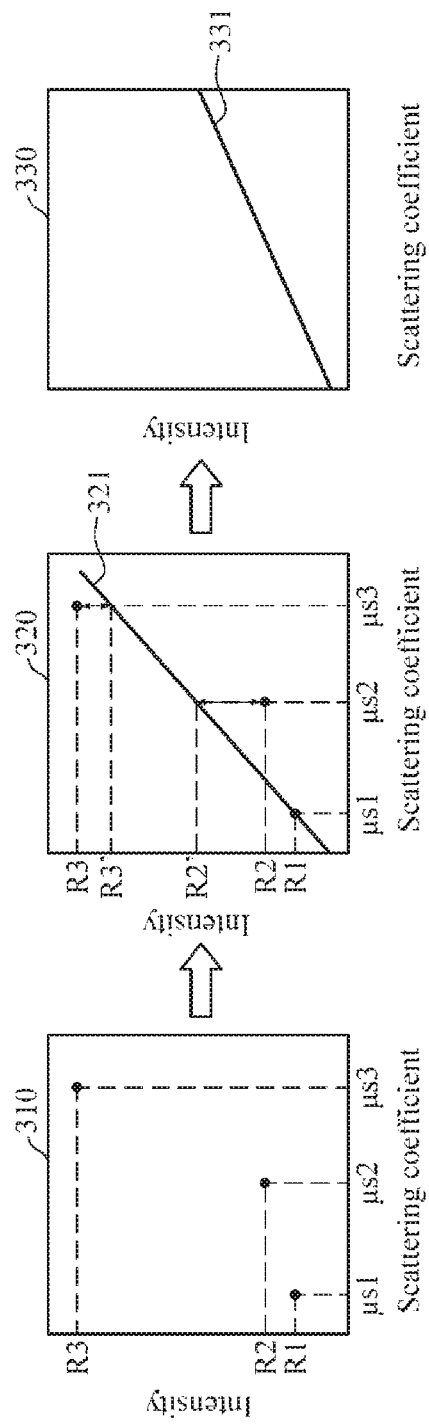
FIG. 3 is a diagram for describing a photodetector-specific representative function correction process.

FIG. 3 is a diagram for describing a photodetector-specific representative function correction process. Hereinafter, the representative function correction process will be described with respect to one photodetector PD1. However, this is for convenience of description, and the representative function correction process can be performed for all the photodetectors constituting a photodetector array. Reference numeral 310 denotes a graph showing the intensity measured at the photodetector PD1 according to the change in scattering coefficient of a subject, reference numeral 320 denotes a graph showing a representative function and an error calculated based on a measured intensity of the photodetector PD1, and reference numeral 330 denotes a graph representing a corrected representative function.

Referring to FIGS. 2 and 3, the photodetector PD1 measures intensity R1 when the scattering coefficient of the subject is µs1, measures intensity R2 when the scattering coefficient of the subject is µs2, and measures intensity R3 when the scattering coefficient of the subject is µs3.

The representative function calculator 210 may calculate the representative function 321, y=ax+b, of the photodetector PD1 through a regression analysis with the scattering coefficients μs1, μs2 and μs3 as dependent variables and the measured intensities R1, R2 and R3 as independent variables.

The error calculator 220 may calculate a predicted intensity R1' (R1'=(μs1−b)/a) for a scattering coefficient of μs1, a predicted intensity R2' (R2'=(μs2−b)/a) for a scattering coefficient of μs2, and a predicted intensity R3' (R3'=(μs3−b)/a) for a scattering coefficient of μs3 by using the representative function y=ax+b. In addition, the error calculator 220 compares the intensities measured for each scattering coefficient with the predicted intensities and calculates an error of 0 (|R1'−R1|=0) when the scattering coefficient is μs1, an error |R2'−R2| when the scattering coefficient is μs2, and an error |R3'−R3| when the scattering coefficient is μs3. In addition, the error calculator 220 calculates an error (|R2'−R2|+|R3'−R3|) of the photodetector PD by summing all the scattering-coefficient-specific errors.

The error corrector 230 corrects the slope of the representative function by subtracting the error of |R2'−R2|+|R3'−R3| from a slope of a of the representative function or by dividing the slope of a of the representative function by the error of |R2'−R2|+|R3'−R3|. Reference numeral 331 in FIG. 3 denotes a corrected representative function of the photodetector PD1.

Figure 4:
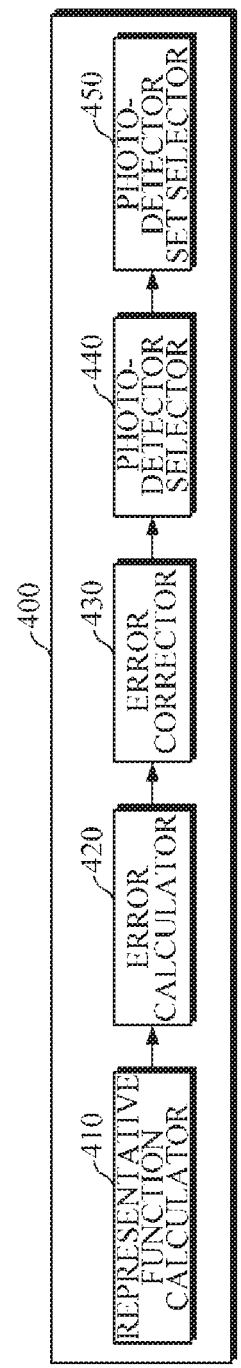
FIG. 4 is a block diagram illustrating another embodiment of the processor.

FIG. 4 is a block diagram illustrating another embodiment of the processor. A processor 400 of FIG. 4 may be another embodiment of the processor 130 of FIG. 1.

Referring to FIG. 4, the processor 400 includes a representative function calculator 410, an error calculator 420, an error corrector 430, an average slope calculator 440, and a photodetector set selector 450.

The representative function calculator 410 may calculate a photodetector-specific representative function that represents a change in measured intensity of each photodetector, on the basis of the change in scattering coefficient of a subject and the corresponding change in the measured intensity of each photodetector. According to an exemplary embodiment, the representative function calculator 410 may calculate a regression equation for the change in measured intensity of each photodetector through a regression analysis and use the calculated regression equation as the representative function of the photodetector.

The error calculator 420 may calculate a photodetector-specific measurement error.

According to an exemplary embodiment, the error calculator 420 may compare the intensities measured by each photodetector for each scattering coefficient with intensities obtained from the representative function of the photodetector to calculate scattering-coefficient-specific errors of each photodetector, and calculate the photodetector-specific measurement error by summing the calculated scattering-coefficient-specific errors of each photodetector.

The error corrector 430 may correct the photodetector-specific representative function using the photodetector-specific measurement error.

For example, the error corrector 430 may correct the photodetector-specific representative function by subtracting the photodetector-specific measurement error from a slope of the photodetector-specific representative function or by dividing the slope of the photodetector-specific representative function by the photodetector-specific measurement error.

The average slope calculator 440 may divide a photodetector array into a plurality of photodetector sets according to a distance from a light source, and calculate an average slope of each of the photodetector sets (hereinafter referred to as a "photodetector-set average slope") by averaging the slopes of corrected representative functions of photodetectors in each of the photodetector sets.

For example, when the photodetector array includes two photodetectors PD1 and PD2 having a distance of ρ1 from the light source, three photodetectors PD3, PD4, and PD5 having a distance of ρ2 from the light source, and four photodetectors PD6, PD7, PD8, and PD9 having a distance of ρ3 from the light source, the average slope calculator 440 may divide the photodetectors PD1 and PD2 into a photodetector set A, the photodetectors PD3 to PD5 into a photodetector set B, and the photodetectors PD6 to PD9 into a photodetector set C. In addition, the average slope calculator 440 may calculate an average slope of the photodetector set A by averaging slopes of the corrected representative functions of the photodetectors PD1 and PD2, calculate an average slope of the photodetector set B by averaging slopes of the corrected representative functions of the photodetectors PD3 to PD5, and calculate an average slope of the photodetector set C by averaging slopes of the corrected representative functions of the photodetectors PD6 to PD9.

The photodetector set selector 450 may select two photodetector sets to be used in measuring a scattering coefficient from the photodetector array on the basis of the average slope of each of the photodetector sets.

According to an exemplary embodiment, the photodetector set selector 450 may select a photodetector set (hereinafter referred to as a "first photodetector set") having the largest positive average slope and a photodetector set (hereinafter referred to as a "second photodetector set") having the largest negative average slope. For example, when the photodetector array includes three photodetector sets A, B, and C, the average slope of the photodetector set A is +6, the average slope of the photodetector set B is +2, and the average slope of the photodetector set C is −1, the photodetector set selector 450 may select the photodetector set A having the largest positive average slope (+6) and the photodetector set C having the largest negative average slope (−1) to be used in measuring a scattering coefficient.

According to an exemplary embodiment, a distance between the light source and the first photodetector set may be shorter than a distance between the light source and the second detector set. That is, the photodetector set selector 450 may select the first photodetector set having the largest positive average slope at a distance close to the light source and select the second photodetector set having the largest negative average slope at a distance far from the light source. However, the description given above is merely one embodiment, and aspects of the present disclosure are not limited thereto. That is, the distance between the light source and the first photodetector set may be greater than the distance between the light source and the second photodetector set according to the performance and use of a system.

Figure 5:
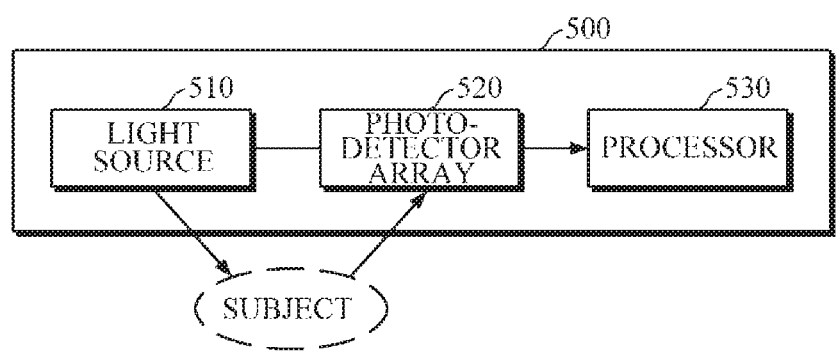
FIG. 5 is a block diagram illustrating one embodiment of a scattering coefficient measurement apparatus.

FIG. 5 is a block diagram illustrating one embodiment of a scattering coefficient measurement apparatus. A scattering coefficient measurement apparatus 500 is an apparatus which selects a photodetector to be used in measuring a scattering coefficient from a plurality of photodetectors and measures a scattering coefficient of a subject using the selected photodetector, and may be mounted in an electronic device. The electronic device may include a mobile phone, a smartphone, a tablet computer, a notebook computer, a PDA, a PMP, a navigation system, an MP3 player, a digital camera, and a wearable device, and the wearable device may include various types, such as a wristwatch type, a wrist band type, a ring type, a belt type, a necklace type, an ankle band type, a thigh band type, a forearm band type, and the like. However, the electronic device and the wearable device are not limited to the aforementioned examples.

Referring to FIG. 5, the scattering coefficient measurement apparatus 500 includes a light source 510, a photodetector array 520, and a processor 530.

The light source 510 may emit light to a subject. For example, the light source 510 may emit light of a predetermined wavelength, for example, NIR, to the subject. However, the wavelength of light to be emitted from the light source 510 may vary according to the measurement purpose or the type of constituent element to be measured. In addition, the light source 510 may not necessarily be configured with a single light emitting object and may be configured with a set of a plurality of light emitting objects. In the case in which the light source 510 is configured with a set of a plurality of light emitting objects, the plurality of light emitting objects may each emit light of a different wavelength or light of the same wavelength according to the measurement purpose. According to an exemplary embodiment, the light source 510 may be an LED or a laser diode, but aspects of the present disclosure are not limited thereto.

The photodetector array 520 may include a plurality of photodetectors. Each of the photodetectors may detect light reflected or scattered from the subject and measure intensity of the detected light. According to an exemplary embodiment, the photodetector may include a photodiode, a photo transistor (PTr), or a CCD.

The processor 530 may select a plurality of photodetectors to be used in measuring a scattering coefficient from the photodetector array 520 on the basis of a change in the intensity measured by each of the photodetectors according to the change in scattering coefficient.

According to an exemplary embodiment, the processor 530 may select, from the photodetector array 520, a first photodetector whose measured intensity increases the most when a scattering coefficient of the subject changes, and a second photodetector whose measured intensity decreases the most when the scattering coefficient of the subject changes. The detailed description of this process is the same as that described above with reference to FIG. 2, and thus will not be reiterated.

According to another embodiment, the processor 530 may divide the photodetector array 520 into a plurality of photodetector sets according to a distance from the light source 510, and may select, from the plurality of photodetector sets, a first photodetector set whose measured intensity increases the most when the scattering coefficient of the subject changes, and a second photodetector set whose measured intensity decreases the most when the scattering coefficient of the subject changes. The detailed description of this process is the same as that described with reference to FIG. 4, and hence will not be reiterated.

When two photodetectors (or two photodetector sets) to be used in measuring a scattering coefficient are selected, the processor 530 may measure a scattering coefficient of the subject using the selected two photodetectors (or two photodetector sets). For example, the processor 530 may control the light source 510 and the two selected photodetectors (or the selected two photodetector sets) to emit light to the subject, detect the light reflected or scattered from the subject and measure the intensity of the detected light. The processor 530 may measure the scattering coefficient of the subject using the intensities measured at the two selected photodetectors (or selected two photodetector sets). According to an exemplary embodiment, the processor 530 may use Equation 1.

$$\mu_s' = \frac{1}{3\mu_a}\left\{\frac{1}{\rho_2-\rho_1}\ln\frac{\rho_1^2 R(\rho_1)}{\rho_2^2 R(\rho_2)}\right\}^2 \quad (1)$$

Here, $\mu_s'$ represents a scattering coefficient of the subject, $\mu_a$ represents an absorbtion coeefficient of the subject, $\rho_1$ denotes a distance between the light source and the first photodetector (or the first photodetector set), $\rho_2$ denotes a distance between the light source and the second photodetector (or the second photodetector set), $R(\rho_1)$ denotes a measured intensity of the first photodetector (or an average measured intensity of the first photodetector set), and $R(\rho_2)$ denotes a measured intensity of the second photodetector (or an average measured intensity of the second photodetector set).

In the case in which the subject is a human body, the measured scattering coefficient of the subject may be used for analyzing body components, such as blood glucose, cholesterol, and triglycerides, or in the case in which the subject is air or liquid, the measured scattering coefficient may be used for measuring contamination of air or liquid.

Figure 6:
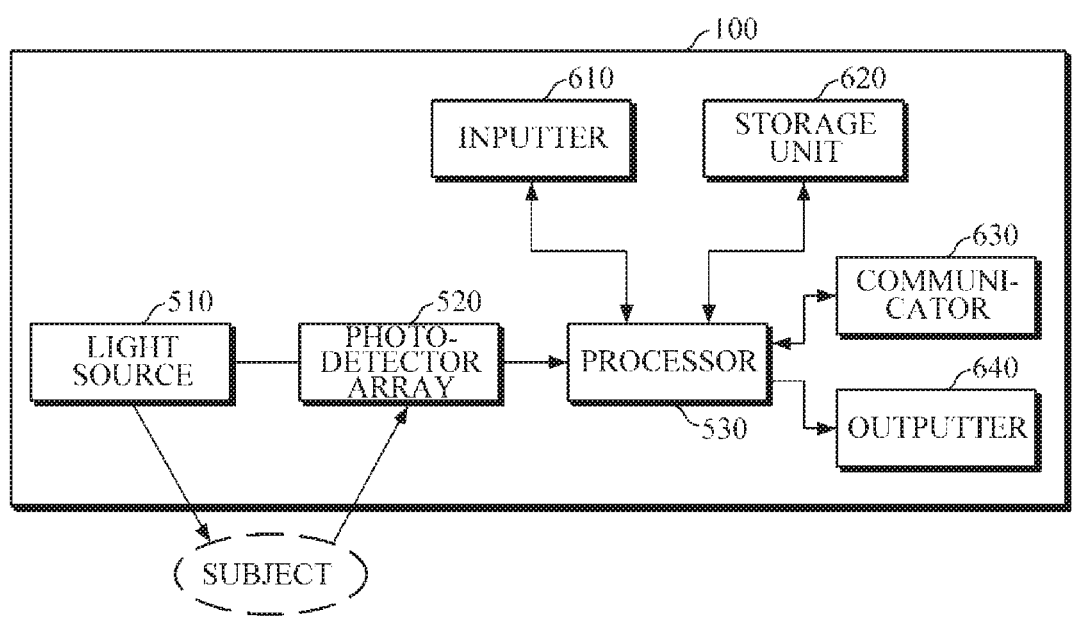
FIG. 6 is a block diagram illustrating another embodiment of the scattering coefficient measurement apparatus.

FIG. 6 is a block diagram illustrating another embodiment of the scattering coefficient measurement apparatus.

Referring to FIG. 6, a scattering coefficient measurement apparatus 600 includes a light source 510, a photodetector array 520, a processor 530, an inputter (e.g., an input interface) 610, a storage unit 620, a communicator (e.g., a communication interface) 630, and an outputter (e.g., an output interface) 640. Here, since the light source 510, the photodetector array 520, and the processor 530 are described with reference to FIG. 5, detailed descriptions thereof will not be reiterated.

The inputter 610 may receive various operation signals from a user. According to an exemplary embodiment, the inputter 610 may include a key pad, a dome switch, a capacitive or resistive touch pad, a jog wheel, a jog switch, a hardware button, and the like. In particular, when the touch pad is configured to form a mutual layer structure with a display, the touch pad and the display may be collectively referred to as a touch screen.

A program or instructions for an operation of the scattering coefficient measurement apparatus 600 and pieces of data to be input to and/or output from the scattering coefficient measurement apparatus 600 may be stored in the storage unit 620. In addition, data about intensity measured at the photodetector array 520, scattering coefficient data of the subject calculated by the processor 530, and the like may be stored in the storage unit 620.

The storage unit 620 may include at least one type of storage medium, such as a flash memory type memory, a hard disk type memory, a multimedia card micro type memory, a card-type memory (e.g., SD or XD memory, etc.) random access memory (RAM), static random access memory (SRAM), read-only memory (ROM), electrically erasable programmable read-only memory (EEPROM), programmable read-only memory, magnetic memory, magnetic disk, and optical disk. In addition, the scattering coefficient measurement apparatus 600 may operate an external storage medium, such as a web storage which performs a storage function of the storage unit 620 on the Internet.

The communicator 630 may communicate with an external device. For example, the communicator 630 may transmit data input from the user through the inputter 610, the measurement data obtained through the photodetector array 520, the scattering coefficient data of the subject calculated by the processor 530, and the like to the external device, or may receive various pieces of data useful for calculating a scattering coefficient of the subject from the external device.

In this case, the external device may be medical equipment using the measured intensity data and/or the calculated scattering coefficient data, a printer to output a result, or a display device to display the measured intensity data and/or the calculated scattering coefficient data. In addition, the external device may be a digital TV, a desktop computer, a mobile phone, a smartphone, a tablet computer, a notebook computer, a PDA, a PMP, a navigation system, an MP3 player, a digital camera, a wearable device, or the like, but is not limited thereto.

The communicator 630 may communicate with the external device using a communication technology, such as Bluetooth communication, Bluetooth low energy (BLE) communication, near field communication (NFC), wireless local area network (WLAN) communication, ZigBee communication, infrared data association (IrDA) communication, Wi-Fi direct (WFD) communication, ultra-wideband (UWB) communication, Ant+ communication, Wi-Fi communication, radio frequency identification (RFID) communication, 3G communication, 4G communication, 5G communication, or the like. However, the description give above is merely an example, and aspects of the present disclosure are not limited thereto.

The outputter 640 may output the intensity data and/or scattering coefficient data. According to an exemplary embodiment, the outputter 640 may output the intensity data and/or the scattering coefficient data using at least one of an audible method, a visual method, and a tactile method. To this end, the outputter 640 may include a display, a speaker, a vibrator, and the like.

Figure 7:
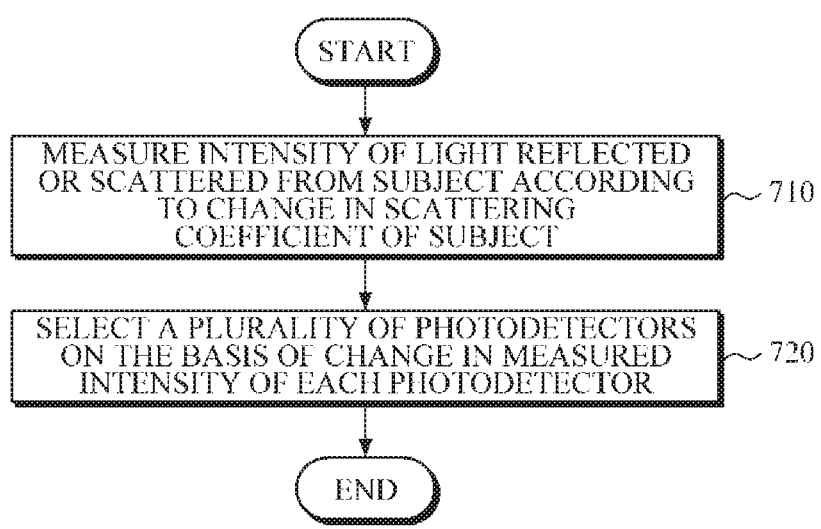
FIG. 7 is a flowchart illustrating one embodiment of a photodetector selection method.

FIG. 7 is a flowchart illustrating one embodiment of a photodetector selection method. A photodetector selection method of FIG. 7 may be performed by the photodetector selection apparatus 100 of FIG. 1.

Referring to FIGS. 1 and 7, each of the photodetectors of the photodetector selection apparatus 100 detects light reflected or scattered from a subject which is irradiated by the light source according to the change in scattering coefficient of the subject and measures intensity of the detected light, as depicted in operation 710.

The photodetector selection apparatus 100 selects a plurality of photodetectors to be used in measuring a scattering coefficient from the photodetector array 120 on the basis of a change in the intensity measured by each of the photodetectors (change in measured intensity of each of the photodetectors) according to the change in scattering coefficient, as depicted in operation 720.

According to an exemplary embodiment, the photodetector selection apparatus 100 may select, from the photodetector array 120, a first photodetector whose measured intensity increases the most when the scattering coefficient of the subject changes, and a second photodetector whose measured intensity decreases the most when the scattering coefficient of the subject changes.

According to another embodiment, the photodetector selection apparatus 100 may divide the photodetector array 120 into a plurality of photodetector sets according to a distance from the light source 110, and may select, from the plurality of photodetector sets, a first photodetector set whose measured intensity increases the most when the scattering coefficient of the subject changes, and a second photodetector set whose measured intensity decreases the most when the scattering coefficient of the subject changes.

Figure 8:
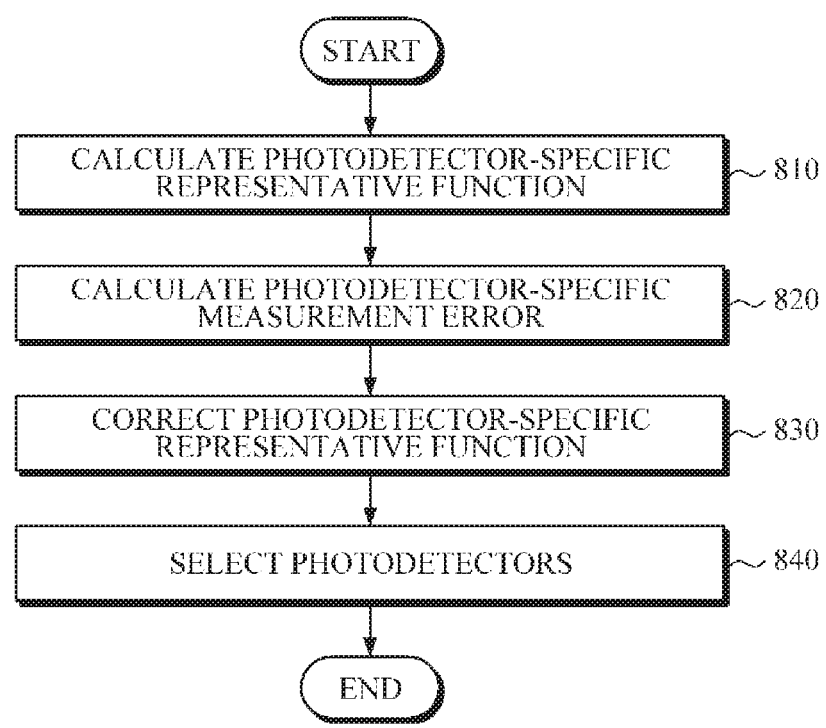
FIG. 8 is a flowchart illustrating one embodiment of photodetector selection operation 720.

FIG. 8 is a flowchart illustrating one embodiment of photodetector selection operation 720.

Referring to FIGS. 1 and 8, the photodetector selection apparatus 100 calculates a photodetector-specific representative function representing the change in the measured intensity of each photodetector according to the change in scattering coefficient, on the basis of the change in the scattering coefficient of the subject and the corresponding change in the measured intensity of each photodetector, in operation 810. According to an exemplary embodiment, the photodetector selection apparatus 100 may calculate a regression equation for the change in measured intensity of each photodetector through a regression analysis and use the calculated regression equation as the representative function of the photodetector.

The photodetector selection apparatus 100 calculates a photodetector-specific measurement error for the photodetector-specific representative function, in operation 820. In this case, the extent that the measured intensity of each photodetector deviates from the linearity of the representative function may be defined as the photodetector-specific measurement error for the photodetector-specific representative function.

The photodetector selection apparatus 100 corrects the photodetector-specific representative function using the photodetector-specific measurement error, as depicted in operation 830. For example, the photodetector selection apparatus 100 may correct the photodetector-specific representative function by subtracting the photodetector-specific measurement error from a slope of the photodetector-specific representative function or by dividing the slope of the photodetector-specific representative function by the photodetector-specific measurement error.

The photodetector selection apparatus 100 selects two photodetectors used in measuring a scattering coefficient from the photodetector array 120 on the basis of the corrected photodetector-specific representative functions, in operation 840. For example, the photodetector selection apparatus 100 may select a first photodetector having the largest positive slope of a photodetector-specific representative function and a second photodetector having the largest negative slope of a photodetector-specific representative function.

Meanwhile, a distance between the light source and the first photodetector may be shorter than a distance between the light source and the second photodetector. That is, photodetector selection apparatus 100 may select the first photodetector, which has the largest positive slope of the corrected representative function, at a distance close to the light source and select the second photodetector, which has the largest negative slope of the corrected representative function, at a distance far from the light source. However, the description given above is merely one embodiment, and aspects of the present disclosure are not limited thereto. That is, the distance between the light source and the first photodetector may be greater than the distance between the light source and the second photodetector according to the performance and use of the system.

Figure 9:
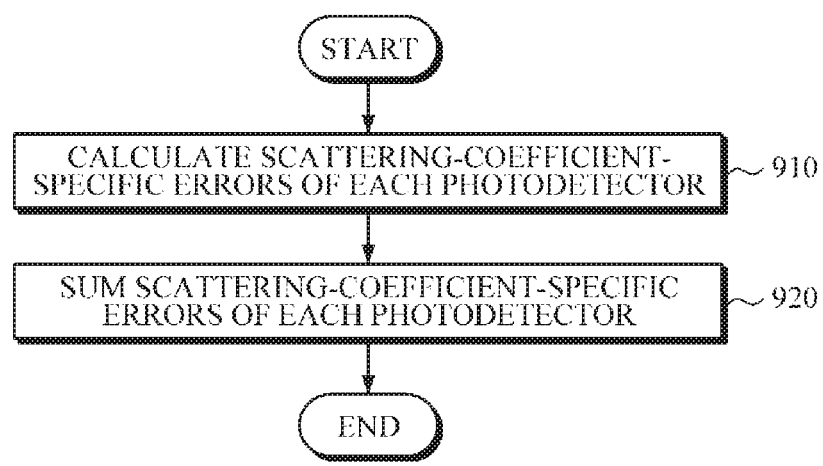
FIG. 9 is a flowchart illustrating one embodiment of photodetector-specific measurement error calculation operation 820.

FIG. 9 is a flowchart illustrating one embodiment of photodetector-specific measurement error calculation operation 820.

Referring to FIGS. 1 and 9, the photodetector selection apparatus 100 compares the intensities measured by each photodetector for each scattering coefficient with intensities obtained from the representative function of the photodetector to calculate scattering-coefficient-specific errors of each photodetector, in operation 910, and calculates the photodetector-specific measurement error by summing the calculated scattering-coefficient-specific errors of each photodetector, in operation 920. For example, under the assumption that, when scattering coefficients of a subject are μs1, μs2, and μs3, intensities measured by a photodetector PD1 are R1, R2, and R3 and predicted intensities obtained through the representative function of the photodetector PD1 are R1', R2', and R3', the photodetector selection apparatus 100 may calculate error E1 (E1=|R1'−R1|) for scattering coefficient μs1, error E2 (E2=|R2'−R2|) for scattering coefficient μs2, and error E3 (E3=|R3'−R3|) for scattering coefficient μs3, and calculate a measurement error Ea(=E1+E2+E3) of the photodetector PD1. Such an error calculation process may be performed for each of the photodetectors in the photodetector array.

Figure 10:
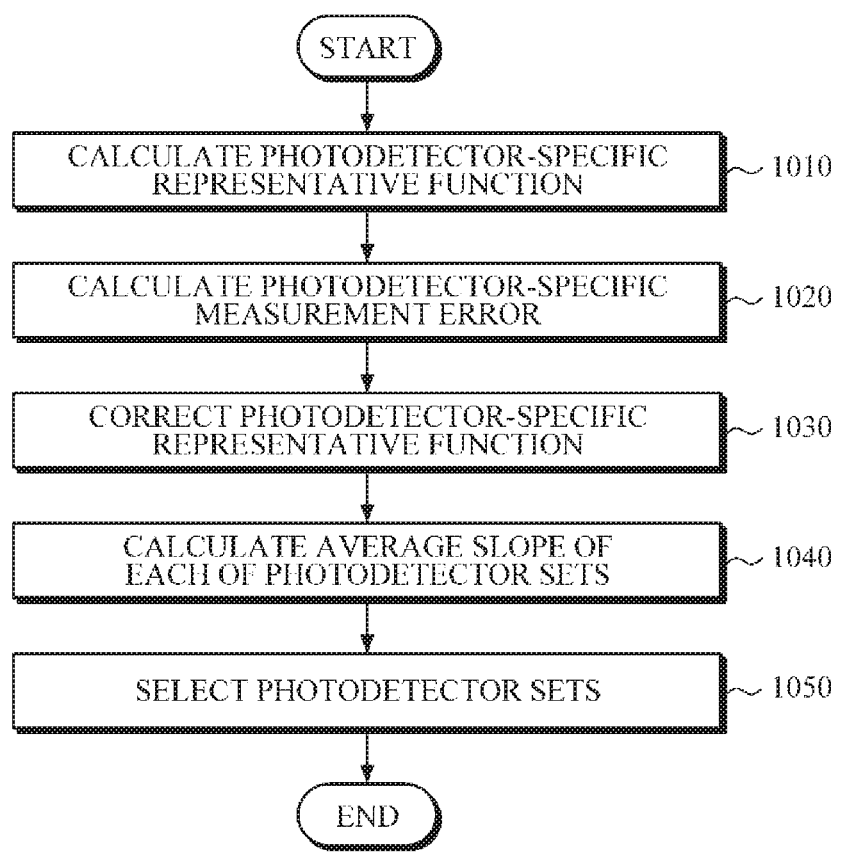
FIG. 10 is a flowchart illustrating another embodiment of photodetector selection operation 720.

FIG. 10 is a flowchart illustrating another embodiment of photodetector selection operation 720.

Referring to FIGS. 1 and 10, the photodetector selection apparatus 100 calculates a photodetector-specific representative function that represents a change in measured intensity of each photodetector, on the basis of the change in scattering coefficient of a subject and the corresponding change in the measured intensity of each photodetector, in operation 1010. For example, the photodetector selection apparatus 100 may calculate a regression equation for the change in measured intensity of each photodetector through a regression analysis and use the calculated regression equation as the representative function of the photodetector.

The photodetector selection apparatus 100 calculates a photodetector-specific measurement error, in operation 1020.

The photodetector selection apparatus 100 corrects the photodetector-specific representative function using the photodetector-specific measurement error, in operation 1030. For example, the photodetector selection apparatus 100 may correct the photodetector-specific representative function by subtracting the photodetector-specific measurement error from a slope of the photodetector-specific representative function or by dividing the slope of the photodetector-specific representative function by the photodetector-specific measurement error.

The photodetector selection apparatus 100 may divide the photodetector array 120 into a plurality of photodetector sets according to a distance from a light source, and calculate a photodetector-set average slope by averaging the slopes of corrected representative functions of photodetectors in each of the photodetector sets, in operation 1040.

The photodetector selection apparatus 100 selects two photodetector sets to be used in measuring a scattering coefficient from the photodetector array on the basis of the photodetector-set average slope, in operation 1050.

According to an exemplary embodiment, the photodetector selection apparatus 100 may select a first photodetector set having the largest positive average slope and a second photodetector set having the largest negative average slope.

Meanwhile, a distance between the light source and the first photodetector set may be shorter than a distance between the light source and the second detector set. That is, the photodetector selection apparatus 100 may select the first photodetector set having the largest positive average slope at a distance close to the light source and select the second photodetector set having the largest negative average slope at a distance far from the light source. However, the description given above is merely one embodiment, and aspects of the present disclosure are not limited thereto. That is, the distance between the light source and the first photodetector set may be greater than the distance between the light source and the second photodetector set according to the performance and use of the system.

Figure 11:
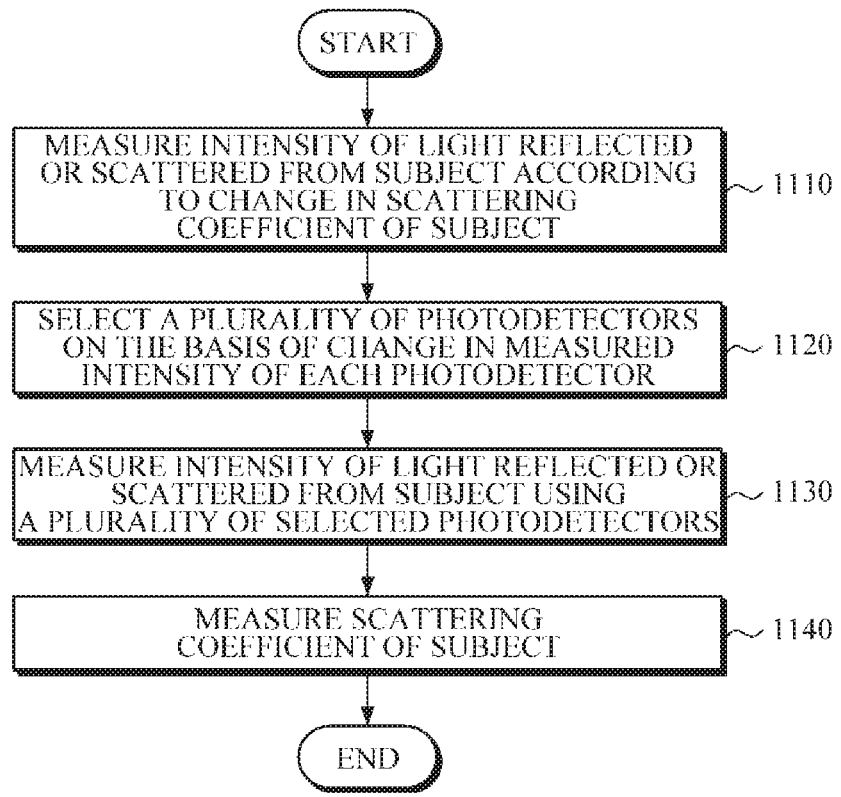
FIG. 11 is a flowchart illustrating one embodiment of a scattering coefficient measurement method.

FIG. 11 is a flowchart illustrating one embodiment of a scattering coefficient measurement method. A scattering coefficient measurement method of FIG. 11 may be performed by the scattering coefficient measurement apparatus 500 of FIG. 5.

Referring to FIGS. 5 and 11, each of the photodetectors of the scattering coefficient measurement apparatus 500 detects light reflected or scattered from a subject which is irradiated by the light source according to the change in scattering coefficient of the subject and measures intensity of the detected light, in operation 1110.

The scattering coefficient measurement apparatus 500 selects a plurality of photodetectors to be used in measuring a scattering coefficient from the photodetector array 520 on the basis of a change in the intensity measured by each of the photodetectors (change in measured intensity of each of the photodetectors) according to the change in scattering coefficient, in operation 1120. According to an exemplary embodiment, the scattering coefficient measurement apparatus 500 may select, from the photodetector array 520, a first photodetector whose measured intensity increases the most when the scattering coefficient of the subject changes, and a second photodetector whose measured intensity decreases the most when the scattering coefficient of the subject changes. According to another embodiment, the scattering coefficient measurement apparatus 500 may divide the photodetector array 520 into a plurality of photodetector sets according to a distance from the light source 510, and may select, from the plurality of photodetector sets, a first photodetector set whose measured intensity increases the most when the scattering coefficient of the subject changes, and a second photodetector set whose measured intensity decreases the most when the scattering coefficient of the subject changes.

The scattering coefficient measurement apparatus 500 may measure the intensity of the light that is reflected or scattered from the subject using the selected first and second photodetector sets, in operation 1130.

The scattering coefficient measurement apparatus 500 measures the scattering coefficient of the subject based on the light intensity measured by the selected first and second photodetector sets, in operation 1140. For example, the scattering coefficient selection apparatus 500 may control the light source 510 and two selected photodetectors (or selected two photodetector sets) to emit light to the subject, detect the light reflected or scattered from the subject and measure the intensity of the detected light, and may measure the scattering coefficient of the subject using the intensities measured at the two selected photodetectors (or two selected photodetector sets). In this case, the scattering coefficient measurement apparatus 500 may use the above-described Equation 1.

In the case in which the subject is a human body, the measured scattering coefficient of the subject may be used for analyzing body components, such as blood glucose, cholesterol, and triglycerides, or in the case in which the subject is air or liquid, the measured scattering coefficient may be used for measuring contamination of air or liquid.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A photodetector selection apparatus for measuring a scattering coefficient, the photodetector selection apparatus comprising:
a light source configured to emit light to a subject;
a photodetector array configured to detect the light that is reflected or scattered from the subject and measure a light intensity of the detected light; and
a processor configured to select at least one photodetector from a plurality of photodetectors of the photodetector array, based on a change in the measured light intensity of each of the plurality of photodetectors according to a change in a scattering coefficient of the subject, and determine the scattering coefficient of the subject based on the light intensity that is measured by the selected at least one photodetector.

2. The photodetector selection apparatus of claim 1, wherein the processor selects a first photodetector and a second photodetector from the plurality of photodetectors,
an increased amount of the measured light intensity of the first photodetector, which is measured while the scattering coefficient changes, is greater than an increased amount of the measured light intensity of any other photodetector in the photodetector array, and
a decreased amount of the measured light intensity of the second photodetector, which is measured while the scattering coefficient changes, is greater than a decreased amount of the measured light intensity of any other photodetector in the photodetector array.

3. The photodetector selection apparatus of claim 2, wherein the processor calculates a photodetector-specific representative function that represents the change in the measured light intensity of each of the plurality of photodetectors, calculates a photodetector-specific measurement error for the photodetector-specific representative function, corrects the photodetector-specific representative function based on the calculated photodetector-specific measurement error, and selects the first photodetector and the second photodetector from the photodetector array based on the corrected photodetector-specific representative function.

4. The photodetector selection apparatus of claim 3, wherein the processor calculates the photodetector-specific representative function through a regression analysis.

5. The photodetector selection apparatus of claim 3, wherein the photodetector-specific measurement error for the photodetector-specific representative function is an extent that a measured light intensity of each specific photodetector deviates from a linearity of a representative function of the specific photodetector.

6. The photodetector selection apparatus of claim 3, wherein the processor calculates scattering-coefficient-specific errors of each of the plurality of photodetectors by comparing intensities measured by each of the plurality of photodetectors for each scattering coefficient with intensities obtained through a representative function of a corresponding photodetector, and calculates the photodetector-specific measurement error by summing the scattering-coefficient-specific errors of each of the plurality of photodetectors.

7. The photodetector selection apparatus of claim 3, wherein the processor corrects a slope of the photodetector-specific representative function based on the calculated photodetector-specific measurement error.

8. The photodetector selection apparatus of claim 7, wherein the processor corrects the slope of the photodetector-specific representative function by subtracting the photodetector-specific measurement error from the slope of the photodetector-specific representative function or by dividing the slope of the photodetector-specific representative function by the photodetector-specific measurement error.

9. The photodetector selection apparatus of claim 3, wherein the processor selects a photodetector having a greatest positive slope of a photodetector-specific representative function as the first photodetector and a photodetector having a greatest negative slope of a photodetector-specific representative function as the second photodetector.

10. The photodetector selection apparatus of claim 9, wherein a distance between the light source and the first photodetector is shorter than a distance between the light source and the second photodetector.

11. The photodetector selection apparatus of claim 1, wherein the processor divides the photodetector array into a plurality of photodetector sets according to a distance from the light source, and selects, from the plurality of photodetector sets, a first photodetector set and a second photodetector set,
an increased amount of the measured light intensity of the first photodetector set, which is measured while the scattering coefficient changes, is greater than an increased amount of the measured light intensity of any other photodetector set in the photodetector array, and
a decreased amount of the measured light intensity of a second photodetector set, which is measured while the scattering coefficient changes, is greater than a decreased amount of the measured light intensity of any other photodetector set in the photodetector array.

12. The photodetector selection apparatus of claim 11, wherein the processor calculates a photodetector-specific representative function that represents the change in the measured light intensity of each of the plurality of photodetectors, calculates a photodetector-specific measurement error for the photodetector-specific representative function, corrects a slope of the photodetector-specific representative function based on the calculated photodetector-specific measurement error, divides the photodetector array into a plurality of photodetector sets according to a distance from the light source, calculates an average slope of each of the plurality of photodetector sets by averaging slopes of corrected photodetector-specific representative functions of photodetectors in each of the plurality of photodetector sets, and selects a first photodetector set and a second photodetector set from the photodetector array based on the calculated average slope of each of the plurality of photodetector sets.

13. The photodetector selection apparatus of claim 12, wherein the processor selects a photodetector set having a greater positive average slope as the first photodetector set and selects a photodetector set having a greatest negative average slope as the second phothodetector set.

14. The photodetector selection apparatus of claim 13, wherein a distance between the light source and the first photodetector set is shorter than a distance between the light source and the second photodetector set.

15. A photodetector selection method for calculating a scattering coefficient, the photodetector selection method comprising:
measuring, by each of a plurality of photodetectors, a light intensity of a light that is emitted to and then reflected or scattered from a subject; and
selecting at least one photodetector from the plurality of photodetectors for measuring a scattering coefficient from a photodetector array based on a change in the measured light intensity of each of the photodetectors according to a change in a scattering coefficient of the subject.

16. The photodetector selection method of claim 15, wherein the selecting the at least one photodetector includes selecting a first photodetector and a second photodetector from the plurality of photodetectors,
an increased amount of the measured light intensity of the first photodetector, which is measured while the scattering coefficient changes, is greater than a increased amount of the measured light intensity of any other photodetector in the photodetector array, and
a decreased amount of the measured light intensity of the second photodetector, which is measured while the scattering coefficient changes, is greater than a decreased amount of the measured light intensity of any other photodetector in the photodetector array.

17. The photodetector selection method of claim 16, wherein the selecting the plurality of photodetectors includes calculating a photodetector-specific representative function that represents the change in the measured light intensity of each of the plurality of photodetectors, calculating a photodetector-specific measurement error for the photodetector-specific representative function, correcting the photodetector-specific representative function based on the calculated photodetector-specific measurement error, and selecting the first photodetector and the second photodetector from the photodetector array based on the corrected photodetector-specific representative function.

18. The photodetector selection method of claim 17, wherein the calculating the photodetector-specific representative function includes calculating the photodetector-specific representative function through a regression analysis.

19. The photodetector selection method of claim 17, wherein the photodetector-specific measurement error for the photodetector-specific representative function is an extent that a measured light intensity of each specific photodetector deviates from a linearity of a representative function of the specific photodetector.

20. The photodetector selection method of claim 17, wherein the calculating the photodetector-specific measurement error includes calculating scattering-coefficient-specific errors of each of the plurality of photodetectors by comparing intensities measured by each of the plurality of photodetectors for each scattering coefficient with intensities obtained through a representative function of a corresponding photodetector and calculating the photodetector-specific measurement error by summing the scattering-coefficient-specific errors of each of the plurality of photodetectors.

21. The photodetector selection method of claim 17, wherein the correcting the photodetector-specific representative function includes correcting a slope of the photodetector-specific representative function based on the calculated photodetector-specific measurement error.

22. The photodetector selection method of claim 21, wherein the correcting the photodetector-specific representative function includes correcting the slope of the photodetector-specific representative function by subtracting the photodetector-specific measurement error from the slope of the photodetector-specific representative function or by dividing the slope of the photodetector-specific representative function by the photodetector-specific measurement error.

23. The photodetector selection method of claim 17, wherein the selecting the first photodetector and the second photodetector includes selecting a photodetector having a greatest positive slope of a photodetector-specific representative function as the first photodetector and a photodetector having a greatest negative slope of a photodetector-specific representative function as the second photodetector.

24. The photodetector selection method of claim 23, wherein a distance between the light source and the first photodetector is shorter than a distance between the light source and the second photodetector.

25. The photodetector selection method of claim 15, wherein the selecting of the plurality of photodetectors includes dividing the photodetector array into a plurality of photodetector sets according to a distance from the light source, and selecting, from the plurality of photodetector sets, a first photodetector set and a second photodetector set
an increased amount of the measured light intensity of the first photodetector set, which is measured while the scattering coefficient changes, is greater than an increased amount of the measured light intensity of any other photodetector set in the photodetector array, and
a decreased amount of the measured light intensity of a second photodetector set, which is measured while the scattering coefficient changes, is greater than a decreased amount of the measured light intensity of any other photodetector set in the photodetector array.

26. The photodetector selection method of claim 25, wherein the selecting the plurality of photodetectors includes calculating a photodetector-specific representative function that represents the change in the measured light intensity of each of the plurality of photodetectors, calculating a photodetector-specific measurement error for the photodetector-specific representative function, correcting a slope of the photodetector-specific representative function based on the calculated photodetector-specific measurement error, dividing the photodetector array into a plurality of photodetector sets according to a distance from the light source, calculating an average slope of each of the plurality of photodetector sets by averaging slopes of corrected photodetector-specific representative functions of photodetectors in each of the plurality of photodetector sets, and selecting a first photodetector set and a second photodetector set from the photodetector array based on the basis the calculated average slope of each of the plurality of photodetector sets.

27. The photodetector selection method of claim 26, wherein the selecting the first photodetector set and the second photodetector set includes selecting a photodetector set having a greatest positive average slope as the first photodetector set and a photodetector set having a greatest negative average slope as the second photodetector set.

28. The photodetector selection method of claim 27, wherein a distance between the light source and the first photodetector set is shorter than a distance between the light source and the second photodetector set.

* * * * *